United States Patent
Zbinden et al.

(10) Patent No.: US 7,718,679 B2
(45) Date of Patent: May 18, 2010

(54) HETEROARYL CARBOXAMIDES

(75) Inventors: Katrin Groebke Zbinden, Liestal (CH); Wolfgang Haap, Loerrach (DE); Hans Hilpert, Muenchenstein (CH); Bernd Kuhn, Liestal (CH); Narendra Panday, Munich (DE); Fabienne Ricklin, Hombourg (FR)

(73) Assignee: Hoffman-La Roche Inc., Nutley, NJ (US)

( * ) Notice: Subject to any disclaimer, the term of this patent is extended or adjusted under 35 U.S.C. 154(b) by 105 days.

(21) Appl. No.: 11/875,041

(22) Filed: Oct. 19, 2007

(65) Prior Publication Data
US 2008/0103143 A1    May 1, 2008

(30) Foreign Application Priority Data
Oct. 25, 2006   (EP)   .................... 06122944

(51) Int. Cl.
*A61K 31/4245* (2006.01)
*A61K 31/497* (2006.01)
*A61K 31/4427* (2006.01)
*A61K 31/5355* (2006.01)
*C07D 271/06* (2006.01)
*C07D 271/10* (2006.01)

(52) U.S. Cl. .................. 514/364; 514/255.05; 514/301; 514/342; 544/111; 546/268.1; 548/131; 548/143; 549/59; 549/60

(58) Field of Classification Search ............. 514/236.2, 514/255.05, 301, 342, 364; 544/111; 546/268.1, 546/268.4, 269.4; 548/125, 131, 143; 549/59, 549/60
See application file for complete search history.

(56) References Cited

U.S. PATENT DOCUMENTS
2006/0100193 A1 *  5/2006  Zhu et al. .............. 514/210.19

FOREIGN PATENT DOCUMENTS
EP          1 491 535          12/2004
WO     WO 2006/034789          4/2006
WO     WO 2006034789 A1 *      4/2006

OTHER PUBLICATIONS
Cheng et al., Biochem. Pharmacol., 22, pp. 3099-3108 (1973).
Lottenberg et al., Biochim. Biophys Acta, 742(3), pp. 539-557(1983).
Eadie, G.S., J. Biol. Chem., 146, pp. 85-93 (1942).

* cited by examiner

*Primary Examiner*—Yong Chu
(74) *Attorney, Agent, or Firm*—George W. Johnston; Dennis P. Tramaloni; Brian C. Remy

(57) ABSTRACT

The invention is concerned with novel heteroaryl carboxamides of formula (I)

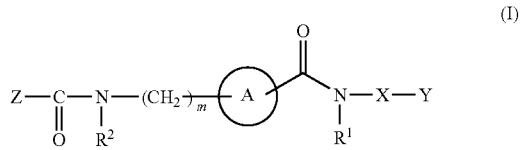

wherein A, $R^1$, $R^2$, X, Y, Z and m are as defined in the description and in the claims, as well as physiologically acceptable salts thereof. These compounds inhibit the coagulation factor Xa and can be used for the treatment or prevention of thrombotic disorders.

16 Claims, No Drawings

HETEROARYL CARBOXAMIDES

PRIORITY TO RELATED APPLICATION(S)

This application claims the benefit of European Patent Application No. 06122944.9, filed Oct. 25, 2006, which is hereby incorporated by reference in its entirety.

BACKGROUND OF THE INVENTION

The invention is concerned with novel heteroaryl carboxamides of formula I and their use as inhibitors of coagulation factor Xa. Factor Xa is a serine endopeptidase composed of two disulfide-linked subunits that converts prothrombin to thrombin in the blood coagulation cascade. Inhibitors of factor Xa can be used for treating thrombotic disorders by inhibiting the formation of thrombin. Prior to the present invention, other inhibitors of factor Xa have been suggested for the inhibition of the formation of thrombin and for the treatment of related diseases. However, there is still a need for novel factor Xa inhibitors which exhibit improved pharmacological properties, i.e., an improved selectivity towards thrombin.

SUMMARY OF THE INVENTION

In sum, the present invention relates to the compounds of formula (I):

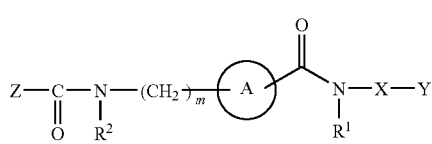

wherein $R^1$, $R^2$, A, X, Y, Z, and m are as defined in the detailed description and in the claims.

The compounds of formula (I) are active compounds and inhibit the coagulation factor Xa. These compounds consequently influence blood coagulation. They therefore inhibit the formation of thrombin and can be used for the treatment and/or prevention of thrombotic disorders, such as amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. They have potential benefit in the treatment of acute vessel closure associated with thrombolytic therapy and restenosis, i.e. after transluminal coronary angioplasty (PTCA) or bypass grafting of the coronary or peripheral arteries and in the maintenance of vascular access patency in long term hemodialysis patients. The compounds of the present invention unexpectedly inhibit coagulation factor Xa and also exhibit improved pharmacological properties compared to other compounds already known in the art. Factor Xa inhibitors of this invention may also form part of a combination therapy with an anticoagulant with a different mode of action or with a platelet aggregation inhibitor or with a thrombolytic agent. Furthermore, these compounds have an effect on tumour cells and prevent metastases. They can therefore also be used as anti-tumour agents.

In addition, the present invention is concerned with a process and an intermediate for the manufacture of the above compounds, pharmaceutical preparations which contain such compounds, the use of these compounds for the production of pharmaceutical preparations as well as a process for the manufacture of the intermediate.

DETAILED DESCRIPTION OF THE INVENTION

Unless otherwise indicated, the following definitions are set forth to illustrate and define the meaning and scope of the various terms used to describe the invention herein.

The term "halogen" or "halo" means fluorine, chlorine, bromine or iodine. Preferred halogens are fluorine, chlorine and bromine, with fluorine and chlorine being more preferred.

The term "$C_{1-6}$alkyl," alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. Preferably, the $C_{1-6}$alkyl is a $C_{1-4}$alkyl (having one to four carbon atoms).

The term "fluoro $C_{1-6}$alkyl" means a $C_{1-6}$alkyl substituted by one or more fluorine atoms. In preferred embodiments the fluoro $C_{1-6}$alkyl is substituted by one, two or three fluorine atoms.

The term "$C_{1-6}$alkoxy," alone or in combination with other groups, means the group R'—O—, wherein R' is a $C_{1-6}$alkyl.

The term "aryl" means phenyl or naphthyl.

The term "arylene" means a divalent aryl group.

The term "phenylene," alone or in combination with other groups, means a divalent phenyl group. 1,4-phenylene is preferred.

The term "heterocyclyl," alone or in combination with other groups, means a non-aromatic mono- or bi-cyclic radical of three to eight ring atoms in which one or two ring atoms are heteroatoms which are N, O or $S(O)_n$ (where n is an integer from 0 to 2), with the remaining ring atoms being carbon atoms.

The term "heterocyclylene," alone or in combination with other groups, means a divalent heterocyclyl group as defined above.

The term "heteroaryl," alone or in combination with other groups, means a monocyclic or bicyclic radical of 5 to 12 ring atoms having at least one aromatic ring containing one, two, or three ring heteroatoms selected from N, O and S, the remaining ring atoms being C, with the understanding that the attachment point of the heteroaryl radical will be on an aromatic ring.

The term "heteroarylene," alone or in combination with other groups, means a divalent heteroaryl group as defined above.

Preferred radicals for the chemical groups whose definitions are given above are those specifically exemplified in the Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" also refers to such salts. Acid addition salts as described above are preferred.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Unless otherwise indicated, the term "a compound of the formula" or "a compound of formula" or "compounds of the formula" or "compounds of formula" means any compound selected from the genus of compounds as defined by the formula.

In detail, the present invention relates to a compound of formula (I):

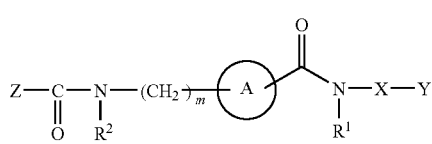

(I)

or a pharmaceutically acceptable salt thereof, wherein:

A is a heteroaryl monocyclic ring of five ring atoms containing one oxygen atom and one or two nitrogen atoms, with the remaining ring atoms being carbon atoms;

$R^1$ is hydrogen or a $C_{1-6}$alkyl;

$R^2$ is hydrogen or a $C_{1-6}$alkyl;

X is selected from the group consisting of: (a) a bond, (b) arylene, (c) heteroarylene, and (d) heterocyclylene, wherein one or two carbon atoms of said heteroarylene or heterocyclylene is optionally replaced with a carbonyl group and wherein said arylene, heteroarylene or heterocyclylene is optionally substituted by one or more substituents independently selected from the group consisting of:
(1) a $C_{1-6}$alkyl,
(2) a $C_{1-6}$alkoxy,
(3) halogen,
(4) cyano,
(5) nitro,
(6) amino,
(7) —N(R')—CO—($C_{1-6}$alkyl optionally substituted by one or more fluorine atoms), in which R' is hydrogen, $C_{1-6}$alkyl or fluoro $C_{1-6}$alkyl,
(8) —N(R')—CO—O—($C_{1-6}$alkyl optionally substituted by one or more fluorine atoms), in which R' is hydrogen, $C_{1-6}$alkyl or fluoro $C_{1-6}$alkyl,
(9) —N(R')—CO—N(R")(R'''), in which R', R" and R''' are independently hydrogen, $C_{1-6}$alkyl or fluoro $C_{1-6}$alkyl,
(10) —C(O)—N(R')(R"), in which R' and R" are independently hydrogen, $C_{1-6}$alkyl or fluoro $C_{1-6}$alkyl, or R' and R", together with the nitrogen atom to which they are attached, form a heterocycyl,
(11) —NR'R", in which R' and R" are independently hydrogen, $C_{1-6}$alkyl or fluoro $C_{1-6}$alkyl, or R' and R", together with the nitrogen atom to which they are attached, form a heterocycyl,
(12)

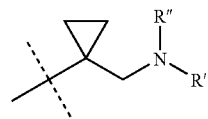

wherein R' and R" are independently $C_{1-6}$alkyl or fluoro $C_{1-6}$alkyl, or R' and R", together with the nitrogen atom to which they are attached, form a heterocyclyl,
(13)

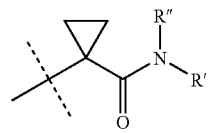

wherein R' and R" are independently $C_{1-6}$alkyl or fluoro $C_{1-6}$alkyl, or R' and R", together with the nitrogen atom to which they are attached, form a heterocyclyl,
(14)

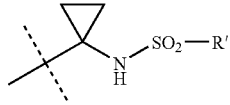

in which R' is fluoro $C_{1-6}$alkyl, and
(15)

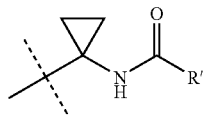

in which R' is fluoro $C_{1-6}$alkyl;

Y is selected from the group consisting of: (a) hydrogen, (b) aryl, (c) heteroaryl, and (d) heterocyclyl, wherein one or two carbon atoms of said heteroaryl and heterocyclyl is optionally replaced with a carbonyl group, and wherein said aryl, heteroaryl and heterocyclyl is optionally substituted by one or more substituents independently selected from the group consisting of:
  (1) a $C_{1-6}$alkyl optionally substituted by one or more fluorine atoms,
  (2) a $C_{1-6}$alkoxy optionally substituted by one or more fluorine atoms,
  (3) halogen,
  (4) cyano,
  (5) nitro,
  (6) amino,
  (7) mono- or di-$C_{1-6}$alkyl substituted amino, in which the $C_{1-6}$alkyl is optionally substituted by one or more fluorine atoms,
  (8) mono- or di-$C_{1-6}$alkyl substituted amino-$C_{1-6}$alkyl, in which the $C_{1-6}$alkyl is optionally substituted by one or more fluorine atoms,
  (9) —$SO_2$-$C_{1-6}$alkyl, in which the $C_{1-6}$alkyl is optionally substituted by one or more fluorine atoms,
  (10) —$SO_2$—$NH_2$, —$SO_2$—NH—$C_{1-6}$alkyl, in which the $C_{1-6}$alkyl is optionally substituted by one or more fluorine atoms, and
  (11) —$SO_2$—N($C_{1-6}$alkyl)$_2$, in which the $C_{1-6}$alkyl is optionally substituted by one or more fluorine atoms;

Z is aryl or heteroaryl, wherein one or two carbon atoms of said heteroaryl is optionally replaced with a carbonyl group; and wherein said aryl or heteroaryl is optionally substituted by one or more substituents independently selected from the group consisting of:
  (1) a $C_{1-6}$alkyl optionally substituted by one or more fluorine atoms,
  (2) a $C_{1-6}$alkoxy optionally substituted by one or more fluorine atoms,
  (3) halogen,
  (4) cyano,
  (5) mono- or di-$C_{1-6}$alkyl substituted amino, in which the $C_{1-6}$alkyl is optionally substituted by one or more fluorine atoms, and
  (6) mono- or di-$C_{1-6}$alkyl substituted amino-$C_{1-6}$alkyl, in which the $C_{1-6}$alkyl is optionally substituted by one or more fluorine atoms, and m is 1 or 2.

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) In the compound of formula (I),
X is preferably a bond or phenylene, said phenylene being optionally substituted by one or more substituents independently selected from the group consisting of $C_{1-6}$alkyl, $C_{1-6}$alkoxy and halogen.
More preferably X is 1,4-phenylene optionally substituted by one substituent selected from the group consisting of halogen and $C_{1-6}$alkyl, and especially X is 2-fluoro-1,4-phenylene.

ii) In the compound of formula (I),
Y is preferably phenyl, heteroaryl or heterocyclyl, said phenyl, heteroaryl and heterocyclyl being optionally substituted by one or more substituents independently selected from the group consisting of $C_{1-6}$alkyl, $C_{1-6}$alkoxy and halogen and one or two carbon atoms of said heteroaryl and heterocyclyl being optionally replaced with a carbonyl group.
More preferably Y is heteroaryl or heterocyclyl, said heteroaryl and heterocyclyl being a mono-cyclic radical of six ring atoms in which one or two ring atoms are heteroatoms selected from N and O, the remaining ring atoms being C, and one carbon atoms of said heteroaryl and heterocyclyl being replaced with a carbonyl group; further more preferably Y is pyridyl, pyrazinyl or morpholinyl, one carbon atoms of said pyridyl, pyrazinyl and morpholinyl being replaced with a carbonyl group; and Y is especially 2-oxo-1-pyridyl,2-oxo-1-pyrazinyl or 3-oxo-4-morpholinyl.

iii) In the compound of formula (I),
Z is preferably heteroaryl optionally substituted by one or more substituents independently selected from the group consisting of $C_{1-6}$alkyl, $C_{1-6}$alkoxy and halogen. More preferably Z is 5-chloro-2-thienyl.

iv) In the compound of formula (I),
A is

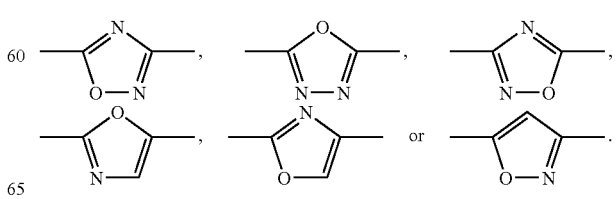

More preferably A is

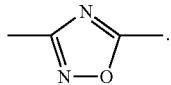

v) In the compound of formula (I), m is preferably 1.

vi) In the compound of formula (I), $R^1$ is preferably hydrogen.

vii) In the compound of formula (I), $R^2$ is preferably hydrogen.

viii) Particularly preferred compounds of the present invention are:

3-{[(5-Chloro-thiophene-2-carbonyl)-amino]-methyl}-[1,2,4]oxadiazole-5-carboxylic acid [2-fluoro-4-(2-oxo-2H-pyridin-1-yl)-phenyl]-amide, 3-{[(5-Chloro-thiophene-2-carbonyl)-amino]-methyl}-[1,2,4]oxadiazole-5-carboxylic acid [2-fluoro-4-(2-oxo-2H-pyrazin-1-yl)-phenyl]-amide, 3-{[(5-Chloro-thiophene-2-carbonyl)-amino]-methyl}-[1,2,4]oxadiazole-5-carboxylic acid [2-fluoro-4-(3-oxo-morpholin-4-yl)-phenyl]-amide or 3-{[(5-Chloro-thiophene-2-carbonyl)-amino]-methyl}-[1,2,4]oxadiazole-5-carboxylic acid [4-(3-oxo-morpholin-4-yl)-phenyl]-amide.

The compounds of the present invention can be prepared, for example, by the general synthetic procedures described below.

General Synthetic Procedures

Abbreviations

BOP: Benzotriazolyl-N-oxy-tris(dimethylamino)-phosphonium hexafluorophosphate

BOP—Cl: Bis-(2-oxo-3-oxazolidinyl)-phosphinic acid chloride

CDI: Carbonyldiimidazole

DCC: N,N'-Dicyclohexylcarbodiimide

DIC: N,N'-Diisopropylcarbodiimide

DIPEA: Diisopropylethylamine

DMA: N,N-Dimethylacetamide

DMF: N,N-Dimethylformamide

EDC: N-(3-Dimetylaminopropyl)-N'-ethyl-carbodiimide hydrochloride

EEDQ: N-Ethoxycarbonyl-2-ethoxy-1,2-dihydroquinoline

HATU: O-(7-Azabenzotriazol-1-yl)-N,N,N',N'-tetramethyluronium hexafluorophosphate HBTU: O-(Benzotriazol-1-yl)-N,N,N',N'-tetramethyluronium hexafluorophosphate HOBt: N-Hydroxybenzotriazole NMP: N-methylpyrrolidone PyBOP: Benzotriazol-1-yl-oxytripyrrolidinephosphonium hexafluorophosphate PyBrOP: Brom-tripyrrolidinophosphonium hexafluorophosphate TBTU: O-(Benzotriazol-1-yl)-N,N,N',N'-tetramethyluronium terafluoroborate THF: Tetrahydrofurane General procedures

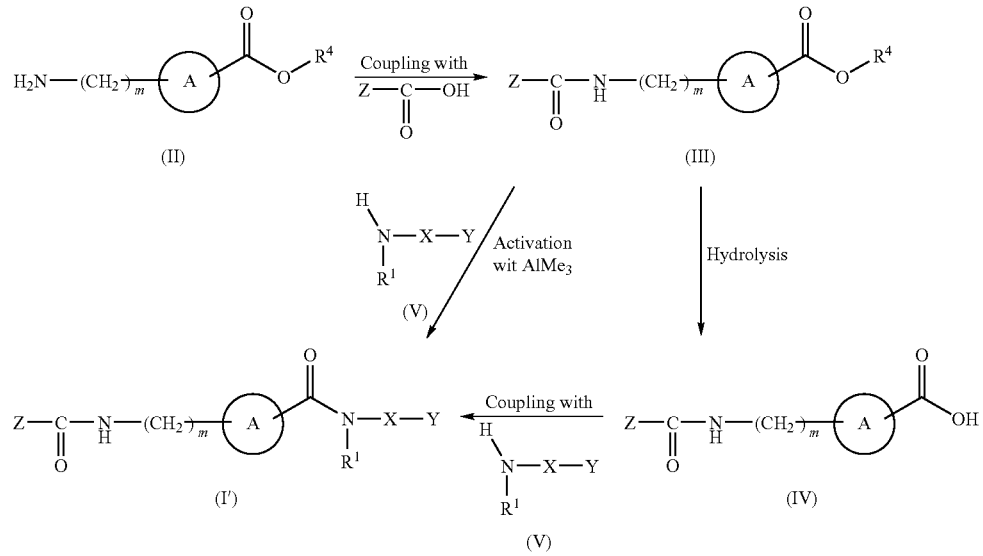

Scheme 1

In scheme 1, A, $R^1$, $R^2$, X, Y, Z and m are as defined before, and $R^4$ is methyl or ethyl. An amine II and an acid Z-COOH can be coupled by reacting the two components in a suitable solvent like dichloromethane, DMF, acetonitrile, THF, NMP, DMA, in the presence of an amide coupling reagent such as EDC, DIC, DCC, CDI, TBTU, HBTU, EEDQ, HOBt, HATU, PyBOP, PyBrOP, BOP or BOP-Cl in the presence of a base like $NEt_3$, hünigs base or N-methylmorpholine at temperatures −20° C. to 120° C. The amide II is obtained after reaction for 0.5-120 h at −20 C. to 120° C. Alternatively, transformation of the acid Z-COOH into the corresponding acid chloride or anhydride by means of oxalyl chloride, thionyl-chloride, isobutylcarbamoyl chloride or related reagents and a base like $NEt_3$, hünigs base, N-methylmorpholine etc, and reaction with the amine II to give the amide III. The preferred conditions involve BOP and DIPEA in DMF at r.t. for 18 hrs.

Saponification of an ester III to give an acid IV is effected by dissolving it in a suitable solvent like MeOH, EtOH, THF, 1,4-dioxane, water or mixtures thereof and a base like LiOH, NaOH, KOH, $Na_2CO_3$, $K_2CO_3$ or $Cs_2CO_3$. Preferred conditions are NaOH in EtOH/$H_2O$.

An acid IV and an amine $HN(R^1)(X—Y)$ can be coupled as described in the preparation of amide III. Preferred conditions are BOP—Cl and DIPEA in acetonitrile/DMF at r.t. for 18 hrs.

Alternatively, an ester III can be directly reacted to an amide I', when $HN(R^1)(X—Y)$ is an aniline. Such anilines are preactivated with $AlMe_3$ in a solvent such as toluene or dioxane at r.t. and subsequently treated with ester III at elevated temperature (usually 90° C.) to give the amide I'.

The starting materials are either commercially available, are otherwise known in the chemical literature, or may be prepared in accordance with methods well known in the art.

As described above, the compounds of formula (I) are active compounds and inhibit the coagulation factor Xa. These compounds consequently influence both platelet activation which is induced by this factor and plasmatic blood coagulation. They therefore inhibit the formation of thrombi and can be used for the treatment and/or prevention of thrombotic disorders, such as, amongst others, arterial and venous thrombosis, deep vein thrombosis, peripheral arterial occlusive disease (PAOD), unstable angina pectoris, myocardial infarction, coronary artery disease, pulmonary embolism, stroke (cerebral thrombosis) due to atrial fibrillation, inflammation and arteriosclerosis. The compounds of the present invention can also be used in the treatment of acute vessel closure associated with thrombolytic therapy and restenosis, i.e. after transluminal coronary angioplasty (PTCA) or bypass grafting of the coronary or peripheral arteries and in the maintenance of vascular access patency in long term hemodialysis patients. F.Xa inhibitors of this invention may form part of a combination therapy with an anticoagulant with a different mode of action or with a platelet aggregation inhibitor or with a thrombolytic agent. Furthermore, these compounds have an effect on tumour cells and prevent metastases. They can therefore also be used as antitumour agents.

Prevention and/or treatment of thrombotic disorders, particularly arterial or deep vein thrombosis, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of diseases which are associated with the coagulation factor Xa, particularly as therapeutically active substances for the treatment and/or prophylaxis of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

In another preferred embodiment, the invention relates to a method for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour, which method comprises administering a compound as defined above to a human being or animal.

The invention also embraces the use of compounds as defined above for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour.

The invention also relates to the use of compounds as described above for the preparation of medicaments for the therapeutic and/or prophylactic treatment of diseases which are associated with the coagulation factor Xa, particularly for the therapeutic and/or prophylactic treatment of thrombotic disorders, arterial thrombosis, venous thrombosis, deep vein thrombosis, peripheral arterial occlusive disease, unstable angina pectoris, myocardial infarction, coronary artery disease, pulmonary embolism, stroke due to atrial fibrillation, inflammation, arteriosclerosis, acute vessel closure associated with thrombolytic therapy or restenosis, and/or tumour. Such medicaments comprise a compound as described above.

The invention also relates to the process and the intermediates for manufacturing the compounds of formula (I) as well as the process for manufacturing the intermediates.

The inhibition of the coagulation factor Xa by the compounds of the present invention can be demonstrated with the aid of a chromogenic peptide substrate assay as described hereinafter.

Factor Xa activity was measured spectrophotometrically in microtiter plates in a final volume of 150 µl using the following conditions: Inhibition of human factor Xa (Enzyme Research Laboratories) was tested at an enzyme concentration of 3 nM using the chromogenic substrate S-2222 (Chromogenix AB, Mölndal, Sweden) at 200 nM. The reaction kinetics of the enzyme and the substrate were linear with both time and the enzyme concentration. The inhibitors were dissolved in DMSO and tested at various concentrations up to 100 µM. The inhibitors were diluted using HNPT buffer consisting of HEPES 100 mMM, NaCl 140 mM, PEG 6000 0.1% and Tween 80 0.02%, pH 7.8. The cleavage of S-2222 by human factor Xa was followed at 405 nm for 5 minutes at room temperature. The velocity of the reaction was determined by the autoreader from the slope of the linear regression fit to 7 time points (1 minute). The initial velocity for each inhibitor concentration was determined by the slope of at least 4 time points in the linear phase by a linear regression fit ($mOD/min^2$). Apparent dissociation constants $K_i$ were calculated according to Cheng and Prusoff [Cheng, Y. C.; Prusoff, W. H. Relationship between the inhibition constant ($K_i$) and the concentration of the inhibitor that causes 50 percent inhibition ($IC_{50}$) of an enzyme reaction. Biochem. Pharmacol. 1973, 22, 3099-3108.] based on the $IC_{50}$ and the respective $K_m$, determined previously ($K_i=IC_{50}/(1+S/K_m)$). The $K_m$ for the substrate used was determined under the conditions of the test with at least 5 substrate concentrations ranging from 0.5 to 15 times $K_m$. [Lottenberg R, Hall J A, Blinder M, Binder E P, Jackson C M. The action of thrombin on peptide p-nitroanilide substrates. Substrate selectivity and examination of hydrolysis under different reaction conditions. Biochim Biophys Acta. Feb. 15, 1983; 742(3):539-57]. According to Eadie [Eadie G. S. The inhibition of cholinesterase by physostigmine and prostigmine. J. Biol. Chem. 1942, 146, 85-93.], the $K_m$ for S-2222 amounted to 613 μM.

The activity of the low molecular weight substances can, moreover, be characterized in the "prothrombin time" (PT) clotting test. The substances are prepared as a 10 mM solution in DMSO and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 μl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 μl of plasma/inhibitor mixture in the measurement container. The clotting reaction was initiated by the addition of 0.1 ml of Dade® Innovin® (recombinant human tissue factor combined with calcium buffer and synthetic phospholipids, Dade Behring, Inc., Cat. B4212-50). The time up to the fibrin cross-linking was determined photooptically from the ACL. The inhibitor concentration, which brought about a doubling of the PT clotting time, was determined by fitting the data to an exponential regression (XLfit).

The compounds of the present invention can furthermore be characterised by the Activated Partial Thromboplastin time (aPTT). This coagulation test can e.g. be run on the ACL 300 Coagulation System (Instrumentation Laboratory) automatic analyzer. The substances are prepared as a 10 mM solution in DMSO and thereafter made up to the desired dilution in the same solvent. The test is performed with the Dade® Actin® FS Activated PTT reagent (purified soy phosphatides in $1.0 \times 10^{-4}$ M ellagic acid, stabilizers and preservative, Dade Behring, Inc., Cat. B4218-100). Thereafter, 0.25 ml aliquots of human plasma (obtained from whole blood anticoagulated with 1/10 volume of 108 mM Na citrate) are spiked with 5 μl of test compound in at least 6 concentrations. 50 μl plasma at 4° C. containing 1/50 vol. inhibitor in solvent are incubated with 50 μl Dade® Actin® FS Activated PTT reagent in water at 37° C. for 3 min., then 50 μl $CaCl_2.2H_2O$ 25 mM in water at 37° C. are added. The time up to the fibrin cross-linking was determined photooptically from the ACL. The inhibitor concentration, which brought about a doubling of the APTT clotting time, was determined by fitting the data to an exponential regression (XLfit).

The $K_i$ values of the active compounds of the present invention preferably amount to about 0.001 to 50 μM, especially about 0.001 to 1 μM. The PT values preferably amount to about 0.5 to 100 μM, especially to about 0.5 to 10 μM. The aPTT values preferably amount to about 0.5 to 100 μM, especially to about 0.5 to 10 μM.

| Example | $K_i$ [μM] factor Xa |
|---------|------|
| Example 1E | 0.005 |
| Example 3 | 0.007 |
| Example 5 | 0.016 |

The compounds of formula (I) and/or their pharmaceutically acceptable salts can be used as medicaments, i.e. in the form of pharmaceutical preparations for enteral, parenteral or topical administration. They can be administered, for example, perorally, i.e. in the form of tablets, coated tablets, dragees, hard and soft gelatine capsules, solutions, emulsions or suspensions, rectally, i.e. in the form of suppositories, parenterally, i.e. in the form of injection solutions or suspensions or infusion solutions, or topically, i.e. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on the severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner. MS=mass spectrometry and $[M+H]^+$=the molecular weight of the compound plus a proton.

EXAMPLES

Example 1

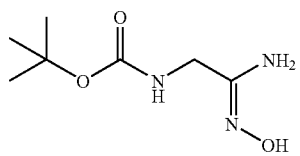

1A

To a stirred solution of N—Boc-2-amino-acetonitrile (4.32 g) at r.t. in ethanol (40 ml) under an argon atmosphere were added H₂O (10 ml), hydroxylamine hydrochloride (1.92 g) and potassium carbonate (3.82 g). The mixture (soon turning to a clear solution) was heated to reflux and stirring was continued for 2 days. The mixture was cooled to r.t. and the ethanol was removed in vacuo.

The brown residue was diluted with H₂O and extracted with EtOAc. The combined organics were washed with brine, dried, filtered and concentrated. The crude (N-hydroxycarbamimidoylmethyl)-carbamic acid tert-butyl ester (3.74 g) was used in the next step without further purification. White solid. MS 190.4 ([M+H]$^{3O}$ )

1B

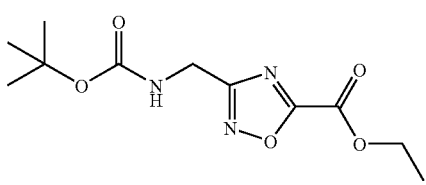

To a stirred solution of (N-hydroxycarbamimidoylmethyl)-carbamic acid tert-butyl ester (2.73 g) at r.t. in ethanol (25 ml) under an argon atmosphere were added NaOEt (290 mg), diethyl oxalate (7.80 g) and pre-dried powdered molecular sieves 4 Å (5.5 g). The mixture was heated to reflux and stirring was continued for 5 hrs. The mixture was cooled to r.t. and filtered. The cake was washed with ethanol. The filtrate was concentrated. The residue was taken up in CH₂Cl₂, washed with sat. aq. NaHCO₃, 2 N HCl, H₂O and brine, dried over MgSO4, filtered and concentrated. The crude product was purified by column chromatography (silica gel; gradient: cyclohexane->cyclohexane/EtOAc 1:1) to give 3-(tert-butoxycarbonylamino-methyl)-[1,2,4]oxadiazole-5-carboxylic acid ethyl ester (1.6 g) as off-white solid. MS 294.3 ([M+H]⁺)

1C

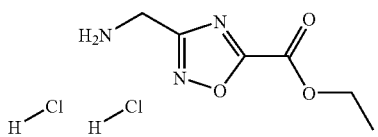

A solution of 3-(tert-butoxycarbonylamino-methyl)-[1,2,4]oxadiazole-5-carboxylic acid ethyl ester (660 mg) in 4 M HCl solution in dioxane (12 ml) was stirred at r.t. under an argon atmosphere for 4 h. The mixture was concentrated. The crude 3-aminomethyl-[1,2,4]oxadiazole-5-carboxylic acid ethyl ester dihydrochloride (562 mg) was used in the next reaction step without further purification. Light yellow gum. MS 172.3 ([M+H]⁺)

1D

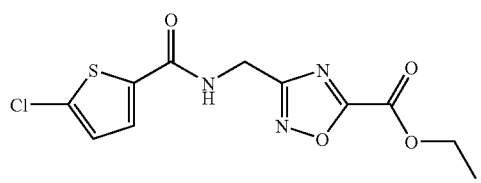

To a stirred solution of 3-aminomethyl-[1,2,4]oxadiazole-5-carboxylic acid ethyl ester dihydrochloride (555 mg) at r.t. in DMF (10 ml) under an argon atmosphere were added N-ethyldiisopropylamine (1.82 ml), 5-chloro-2-thiophenecarboxylic acid (565 mg) and BOP (1.54 mg). The mixture was stirred over night, then diluted with EtOAc and washed with H₂O. The aqueous phase was back extracted with EtOAc and brine, dried over MgSO₄, filtered and concentrated. The crude product was purified by column chromatography (silica gel; gradient: cyclohexane->cyclohexane/EtOAc 1:1) to give 3-{[(5-chloro-thiophene-2-carbonyl)-amino]-methyl}-[1,2,4]oxadiazole-5-carboxylic acid ethyl ester (586 mg) as off-white solid. MS 316.0 ([M+H]⁺)

1E

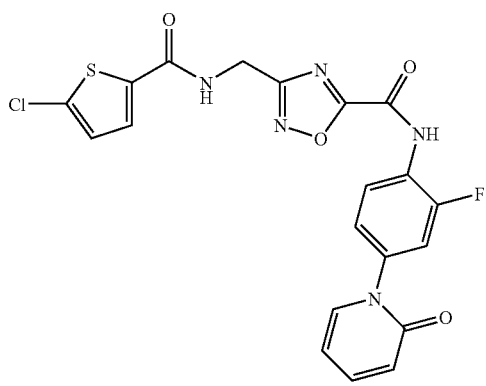

To a stirred suspension of 1-(4-amino-3-fluoro-phenyl)-1H-pyridin-2-one (259 mg; CAS 536747-52-1, prepared according to C. F. Bigge et al., patent application WO 2003045912) at r.t. in dioxane (4 ml) under an argon atmosphere was added trimethylaluminium (0.63 ml; 2 M solution in heptane)-->foaming. The mixture was stirred at r.t. for 2 h. A solution of 3-{[(5-chloro-thiophene-2-carbonyl)-amino]-methyl}-[1,2,4]oxadiazole-5-carboxylic acid ethyl ester (100 mg) in dioxane (4 ml) was then added. The mixture was heated to 100° C. over night. The mixture was cooled to r.t. and H₂O (0.8 ml) was added (-->bubbling). After 15 min stirring, MgSO₄ was added and stirring was continued for another 15 min. The mixture was then filtered and the cake was washed with dichloromethane. The filtrate was concentrated. The crude product was purified by column chromatography (silica gel; gradient: CH₂Cl₂->CH₂Cl₂/MeOH 9:1) to give 3-{[(5-chloro-thiophene-2-carbonyl)-amino]-methyl}-[1,2,4]oxadiazole-5-carboxylic acid[2-fluoro-4-(2-oxo-2H-pyridin-1-yl)-phenyl]-amide as light yellow solid. 474.1 ([M+H]⁺)

Example 2

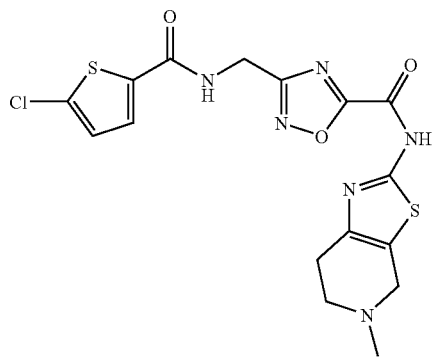

In analogy to example 1E 3-{[(5-chloro-thiophene-2-carbonyl)-amino]-methyl}-[1,2,4]oxadiazole-5-carboxylic acid ethyl ester (example 1D) was reacted with 5-methyl-4,5,6,7-tetrahydro-thiazolo[5,4]pyridin-2-ylamine (CAS 17899-48-8) to give 3{[(5-chloro-thiophene-2-carbonyl)-amino]-methyl}-[1,2,4]oxadiazole-5-carboxylic acid (5-methyl-4,5,6,7-tetrahydro-thiazolo[5,4-c]pyridin-2-yl)-amide. Yellow solid. MS 439.3 ([M+H]⁺)

Example 3

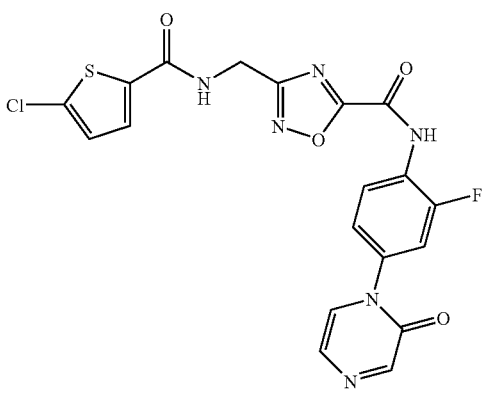

In analogy to example 1E 3-{[(5-chloro-thiophene-2-carbonyl)-amino]-methyl}-[1,2,4]oxadiazole-5carboxylic acid ethyl ester (example 1D) was reacted with 1-(4-amino-3-fluoro-phenyl)-pyrazine-2-one (CAS 863015-77-4) to give 3-{[(5-chloro-thiophene-2-carbonyl)-amino]-methyl}-[1,2,4]oxadiazole-5-carboxylic acid [2-fluoro-4-(2-oxo-2H-pyrazine-1-yl)-phenyl]-amide. Yellow solid. MS 475.0 ([M+H]⁻)

Example 4

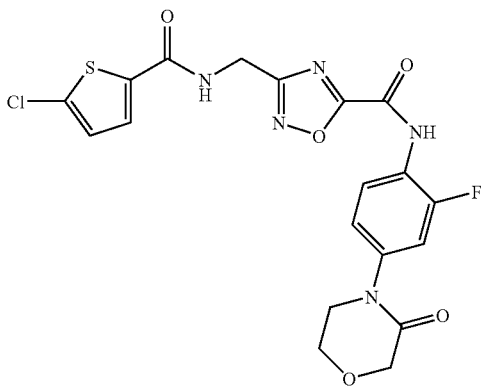

In analogy to example 1E 3-{[(5-chloro-thiophene-2-carbonyl)-amino]-methyl}-[1,2,4]oxadiazole-5-carboxylic acid ethyl ester (example 1D) was reacted with 4-(4-amino-3-fluoro-phenyl)-morpholin-3-one (CAS 742073-22-9) to give 3-{[(5-chloro-thiophene-2-carbonyl)-amino]-methyl}-[1,2,4]oxadiazole-5-carboxylic acid [2-fluoro-4-(3-oxo-morpholin-4-yl)-phenyl]-amide. Light yellow solid. MS 480.0 ([M+H]⁺)

Example 5

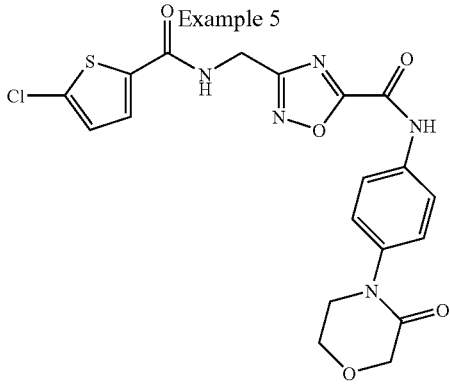

In analogy to example 1E 3-{[(5-chloro-thiophene-2-carbonyl)-amino]-methyl}-[1,2,4]oxadiazole-5-carboxylic acid ethyl ester (example 1D) was reacted with 4-(4-amino-3-fluoro-phenyl)-morpholin-3-one (CAS 438056-69-0) to give 3-{[(5-chloro-thiophene-2-carbonyl)-amino]-methyl}-[1,2,4]oxadiazole-5-carboxylic acid [4-(3-oxo-morpholin-4-yl)-phenyl]-amide. Light yellow solid. MS 462.0 ([M+H]⁻)

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:
1. A compound of formula (I):

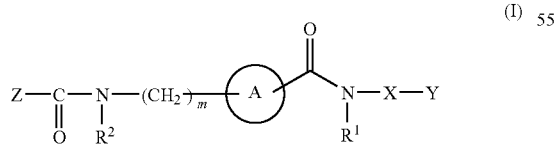

(I)

or a pharmaceutically acceptable salt thereof, wherein:
A is a heteroaryl monocyclic ring of five ring atoms containing one oxygen atom and two nitrogen atoms, with the remaining ring atoms being carbon atoms;
$R^1$ is hydrogen or a $C_{1-6}$ alkyl;
$R^2$ is hydrogen or a $C_{1-6}$ alkyl;

X is selected from the group consisting of: (a) a bond, (b) arylene, (c) heteroarylene, and (d) heterocyclylene, wherein one or two carbon atoms of said heteroarylene or heterocyclylene is optionally replaced with a carbonyl group and wherein said arylene, heteroarylene or heterocyclylene is optionally substituted by one or more substituents independently selected from the group consisting of:
(1) a $C_{1-6}$ alkyl,
(2) a $C_{1-6}$ alkoxy,
(3) halogen,
(4) cyano,
(5) nitro,
(6) amino,
(7) —N(R')—CO—($C_{1-6}$ alkyl optionally substituted by one or more fluorine atoms), in which R' is hydrogen, $C_{1-6}$ alkyl or fluoro $C_{1-6}$ alkyl,
(8) —N(R')—CO—O—($C_{1-6}$ alkyl optionally substituted by one or more fluorine atoms), in which R' is hydrogen, $C_{1-6}$ alkyl or fluoro $C_{1-6}$ alkyl,
(9) —N(R')—CO—N(R")(R'''), in which R', R" and R''' are independently hydrogen, $C_{1-6}$alkyl or fluoro $C_{1-6}$ alkyl,
(10) —C(O)—N(R')(R"), in which R' and R" are independently hydrogen, $C_{1-6}$ alkyl or fluoro $C_{1-6}$ alkyl, or R' and R", together with the nitrogen atom to which they are attached, form a heterocycyl,
(11) —NR'R", in which R' and R" are independently hydrogen, $C_{1-6}$ alkyl or fluoro $C_{1-6}$ alkyl, or R' and R", together with the nitrogen atom to which they are attached, form a heterocycyl,
(12)

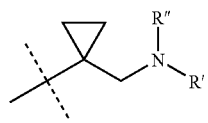

wherein R' and R" are independently $C_{1-6}$ alkyl or fluoro $C_{1-6}$ alkyl, or R' and R", together with the nitrogen atom to which they are attached, form a heterocyclyl,
(13)

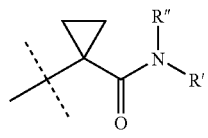

wherein R' and R" are independently $C_{1-6}$ alkyl or fluoro $C_{1-6}$ alkyl, or R' and R", together with the nitrogen atom to which they are attached, form a heterocyclyl,
(14)

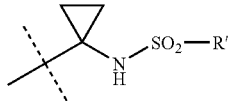

in which R' is fluoro $C_{1-6}$ alkyl, and
(15)

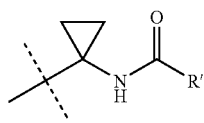

in which R' is fluoro $C_{1-6}$ alkyl;
Y is selected from the group consisting of: (a) hydrogen, (b) aryl, (c) heteroaryl, and (d) heterocyclyl, wherein one or two carbon atoms of said heteroaryl and heterocyclyl is optionally replaced with a carbonyl group, and wherein said aryl, heteroaryl and heterocyclyl is optionally substituted by one or more substituents independently selected from the group consisting of:
(1) a $C_{1-6}$ alkyl optionally substituted by one or more fluorine atoms,
(2) a $C_{1-6}$ alkoxy optionally substituted by one or more fluorine atoms,
(3) halogen,
(4) cyano,
(5) nitro,
(6) amino,
(7) mono- or di-$C_{1-6}$ alkyl substituted amino, in which the $C_{1-6}$ alkyl is optionally substituted by one or more fluorine atoms,
(8) mono- or di-$C_{1-6}$ alkyl substituted amino-$C_{1-6}$ alkyl, in which the $C_{1-6}$ alkyl is optionally substituted by one or more fluorine atoms,
(9) —$SO_2$—$C_{1-6}$ alkyl, in which the $C_{1-6}$ alkyl is optionally substituted by one or more fluorine atoms,
(10) —$SO_2$—$NH_2$, —$SO_2$—NH—$C_{1-6}$ alkyl, in which the $C_{1-6}$ alkyl is optionally substituted by one or more fluorine atoms, and
(11) —$SO_2$—N($C_{1-6}$ alkyl)$_2$, in which the $C_{1-6}$ alkyl is optionally substituted by one or more fluorine atoms;
Z is aryl or heteroaryl, wherein one or two carbon atoms of said heteroaryl is optionally replaced with a carbonyl group; and wherein said aryl or heteroaryl is optionally substituted by one or more substituents independently selected from the group consisting of:
(1) a $C_{1-6}$ alkyl optionally substituted by one or more fluorine atoms,
(2) a $C_{1-6}$ alkoxy optionally substituted by one or more fluorine atoms,
(3) halogen,
(4) cyano,
(5) mono- or di-$C_{1-6}$ alkyl substituted amino, in which the $C_{1-6}$ alkyl is optionally substituted by one or more fluorine atoms, and
(6) mono- or di-$C_{1-6}$ alkyl substituted amino-$C_{1-6}$ alkyl, in which the $C_{1-6}$ alkyl is optionally substituted by one or more fluorine atoms, and
m is 1 or 2.

2. A compound of claim 1, wherein:
X is a bond or phenylene, wherein said phenylene is optionally substituted by one or more substituents independently selected from the group consisting of $C_{1-6}$ alkyl, $C_{1-6}$ alkoxy and halogen; and
Y is phenyl, heteroaryl or heterocyclyl, wherein said phenyl, heteroaryl and heterocyclyl is optionally substituted by one or more substituents independently selected from the group consisting of $C_{1-6}$ alkyl, $C_{1-6}$ alkoxy and halogen and wherein one or two carbon atoms of said heteroaryl and heterocyclyl is optionally replaced with a carbonyl group.

3. A compound of claim 1, wherein:
X is 1,4-phenylene optionally substituted by one substituent selected from the group consisting of halogen and $C_{1-6}$ alkyl.

4. A compound of claim 1, wherein X is 2-fluoro-1,4-phenylene.

5. A compound of claim 1, wherein Y is heteroaryl or heterocyclyl, wherein said heteroaryl or heterocyclyl is a mono-cyclic radical of six ring atoms in which one or two ring atoms are heteroatoms selected from N and O, with the remaining ring atoms being carbon atoms, and one carbon atom of said heteroaryl or heterocyclyl is replaced with a carbonyl group.

6. A compound of claim 1, wherein Y is pyridyl, pyrazinyl or morpholinyl, wherein one carbon atom of said pyridyl, pyrazinyl or morpholinyl is replaced with a carbonyl group.

7. A compound of claim 1 wherein Y is 2-oxo-1-pyridyl, 2-oxo-1-pyrazinyl, or 3-oxo-4-morpholinyl.

8. A compound of claim 1, wherein Z is heteroaryl optionally substituted by one or more substituents independently selected from the group consisting of $C_{1-6}$ alkyl, $C_{1-6}$ alkoxy and halogen.

9. A compound of claim 1, wherein Z is 5-chloro-2-thienyl.

10. A compound of claim 1, wherein A is:

11. A compound of claim 1, wherein A is:

12. A compound of claim 1, wherein m is 1.
13. A compound of claim 1, wherein $R^1$ is hydrogen.
14. A compound of claim 1, wherein $R^2$ is hydrogen.
15. A compound of claim 1, which is selected from the group consisting of:
3-{[(5-Chloro-thiophene-2-carbonyl)-amino]-methyl}-[1,2,4]oxadiazole-5-carboxylic acid [2-fluoro-4-(2-oxo-2H-pyridin-1-yl)-phenyl]-amide,
3-{[(5-Chloro-thiophene-2-carbonyl)-amino]-methyl}-[1,2,4]oxadiazole-5-carboxylic acid [2-fluoro-4-(2-oxo-2H-pyrazin-1-yl)-phenyl]-amide,
3-{[(5-Chloro-thiophene-2-carbonyl)-amino]-methyl}-[1,2,4]oxadiazole-5-carboxylic acid [2-fluoro-4-(3-oxo-morpholin-4-yl)-phenyl]-amide, and
3-{[(5-Chloro-thiophene-2-carbonyl)-amino]-methyl}-[1,2,4]oxadiazole-5-carboxylic acid [4-(3-oxo-morpholin-4-yl)-phenyl]-amide.

16. A pharmaceutical composition comprising a therapeutically effective amount of a compound of claim 1 and a pharmaceutically acceptable carrier.

\* \* \* \* \*